United States Patent
Zetina-Rocha et al.

(10) Patent No.: US 7,087,611 B2
(45) Date of Patent: Aug. 8, 2006

(54) PREPARATION OF AN ANHYDRATE FORM OF 5-[2-[4-(1,2-BENZISOTHIAZOL-3-YL)-1-PIPERAZINYL]ETHYL]-6-CHLORO-1,3-DIHYDRO-2H-INDOL-2-ONE HYDROCHLORIDE (ZIPRASIDONE HYDROCHLORIDE)

(75) Inventors: Carlos Zetina-Rocha, Brantford (CA); Allan W. Rey, Brantford (CA); Stephen E. Horne, Burlington (CA)

(73) Assignee: Apotex Pharmachem Inc., Brantford (CA)

(*) Notice: Subject to any disclaimer, the term of this patent is extended or adjusted under 35 U.S.C. 154(b) by 65 days.

(21) Appl. No.: 10/928,139

(22) Filed: Aug. 30, 2004

(65) Prior Publication Data

US 2005/0277651 A1 Dec. 15, 2005

(30) Foreign Application Priority Data

Jun. 14, 2004 (CA) .................... 2471219

(51) Int. Cl.
C07D 209/34 (2006.01)
C07D 409/14 (2006.01)
C07D 285/01 (2006.01)

(52) U.S. Cl. ................. 514/254.04; 548/456; 548/486; 548/212; 544/368; 544/373

(58) Field of Classification Search ............... 544/368, 544/372; 548/486, 456, 212
See application file for complete search history.

(56) References Cited

U.S. PATENT DOCUMENTS

| 4,831,031 A | * | 5/1989 | Lowe et al. ........... 514/254.02 |
| 5,206,366 A | | 4/1993 | Bowles |
| 5,312,925 A | | 5/1994 | Allen et al. |
| 5,338,846 A | | 8/1994 | Busch et al. |
| 5,935,960 A | | 8/1999 | Walinsky et al. |
| 6,150,366 A | | 11/2000 | Arenson et al. |
| 2004/0152711 A1 | | 8/2004 | Reddy, et al. |

FOREIGN PATENT DOCUMENTS

| CA | 2166203 | 4/2001 |
| CA | 2245269 | 1/2003 |
| CA | 2252898 | 4/2003 |
| WO | WO 950510 | 1/1995 |
| WO | WO 2003/070246 | 8/2003 |
| WO | WO 2004/050655 | 6/2004 |

OTHER PUBLICATIONS

M. B. Smith, Organic Synthesis, 1994, McGraw-Hill, Inc. p. 125.*
J. McMurry, Organic Chemistry, 1988, Brooks/Cole Publishing Company, p. 355.*
Merck Index, 12th edition, 1996, p. 1044.*

* cited by examiner

Primary Examiner—Kamal A. Saeed
Assistant Examiner—Yong Chu
(74) Attorney, Agent, or Firm—Samuel T. Tekie; Ivor M. Hughes; Marcelo K. Sarkis

(57) ABSTRACT

The present invention relates to new and useful processes for the preparation of the anhydrate form of 5-[2-[4-(1,2-benzisothiazol-3-yl)-1-piperazinyl]ethyl]-6-chloro-1,3-dihydro-2H-indol-2-one hydrochloride.

12 Claims, No Drawings

PREPARATION OF AN ANHYDRATE FORM OF 5-[2-[4-(1,2-BENZISOTHIAZOL-3-YL)-1-PIPERAZINYL]ETHYL]-6-CHLORO-1,3-DIHYDRO-2H-INDOL-2-ONE HYDROCHLORIDE (ZIPRASIDONE HYDROCHLORIDE)

This United States Patent Application claims priority from Canadian Patent Application No. 2,471,219 filed Jun. 14, 2004.

Improved preparation of an anhydrate form of 5-[2-[4-(1,2-benzisothiazol-3-yl)-1-piperazinyl]ethyl]-6-chloro-1,3-dihydro-2H-indol-2-one hydrochloride (Ziprasidone hydrochloride).

BACKGROUND OF THE INVENTION

Ziprasidone hydrochloride (5-[2-[4-(1,2-benzisothiazol-3-yl)-1-piperazinyl]ethyl]-6-chloro-1,3-dihydro-2H-indol-2-one hydrochloride), I is a potent neuroleptic agent useful in the treatment of psychotic disorders, schizophrenia, and anxiety diseases. It is currently marketed under the proprietary name of Geodon.

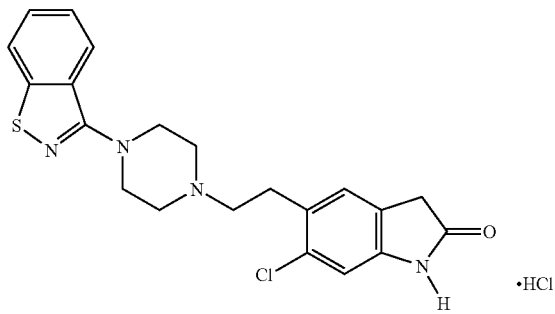

I

Ziprasidone hydrochloride is known to exist in three crystalline forms; namely, the monohydrate, hemihydrate and anhydrous form as disclosed in U.S. Pat. Nos. 4,831,031 and 5,312,925, both of which are herein incorporated by reference. U.S. Pat. No. 5,312,925 states that ziprasidone hydrochloride monohydrate is substantially hygroscopically stable, thus alleviating potential problems due to weight changes of the active pharmaceutical ingredient during the final formulation process. Nevertheless a very low aqueous solubility is observed for this crystalline form.

U.S. Pat. No. 4,831,031 discloses that arylpiperazinyl-ethyl (or butyl)-heterocyclic compounds II may be prepared by reacting piperazines of the formula III with compounds of the formula IV as follows:

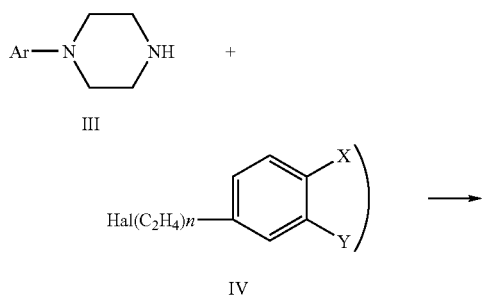

III

IV

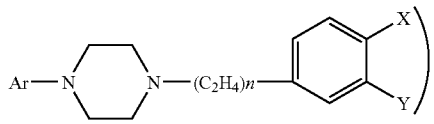

II

The '031 patent indicates that this coupling reaction is generally conducted in a polar solvent, such as a lower alcohol, dimethylformamide or methyl isobutyl ketone, and in the presence of a weak base and that, preferably, the reaction is in the further presence of a catalytic amount of sodium iodide, and a neutralizing agent for hydrochloride such as sodium carbonate. At example 16, the '031 patent discloses a process in which a solution of ziprasidone free base is taken up in dichloromethane and then reacted with ether saturated with HCl to afford a precipitate which is subsequently filtered, slurried with acetone and filtered again to give ziprasidone hydrochoride hemihydrate.

Additionally, the methods described in the prior art for the preparation of some of these crystalline forms, for instance ziprasidone hydrochloride anhydrate provide inconsistent reproducibility. For example, ziprasidone hydrochloride anhydrate has been prepared by prolonged drying in air at 50° C. of the corresponding monohydrate form, as disclosed in U.S. Pat. No. 5,312,925. However, repeated attempts to prepare the anhydrous form of ziprasidone hydrochloride in our laboratory by using the above mentioned conditions failed to produce the expected anhydrate and instead ziprasidone hydrochloride having variable contents of water, including that corresponding to the hemihydrate form, were obtained. Furthermore, even when more drastic conditions were used, (i.e., higher temperatures, longer drying times, under vacuum) anhydrous product was still not obtained.

It is therefore very desirable to have a process for preparing ziprasidone hydrochloride anhydrate which overcomes the deficiencies of the prior art.

It is therefore an object of the present invention to provide an improved process for preparing ziprasidone hydrochloride anhydrate in high yields and purity which is more reliable, consistent and suitable for large scale manufacturing. Further and other aspects of the invention will be realized by those skilled in the art from the following Summary of the Invention and Detailed Description of Embodiments of the Invention.

SUMMARY OF THE INVENTION

Thus, in accordance with an aspect of the present invention there is provided a process for preparing anhydrous ziprasidone hydrochloride comprising the steps of:
(i) (a) dissolving ziprasidone free base in a polar solvent, such as 1-methyl-2-pyrrolidinone (NMP) for example, at a temperature between about 20° C. and about 60° C., or,
(b) suspending ziprasidone free base in a suitable organic solvent or mixture of solvents such as a medium polarity organic solvent or mixtures thereof at, for example, a temperature from about 0° C. to about 60° C.,
(ii) adding hydrogen chloride as a gas or in a suitable organic solvent such as isopropanol, ethyl ether, acetic acid and ethanol;
(iii) stirring the mixture at a temperature between about 0° C. and about 60° C. thereby producing crystals of product, (iv) if required filtering and washing the crystals,
(v) if required, stirring the crystals with a suitable organic solvent at a temperature between about 0° C. and about 60° C.,
(vi) if required, filtering and washing the crystals,
(vii) drying the crystals.

Thus according to another aspect of the invention a process is provided for the preparation of ziprasidone hydrochloride anhydrate comprising the steps of:
(i) mixing ziprasidone free base in a suitable medium polarity to polar organic solvent;
(ii) adding hydrogen chloride;
(iii) stirring the reaction mixture for a sufficient amount of time to obtain complete ziprasidone hydrochloride formation; and thereafter isolating ziprasidone hydrochloride anhydrate and drying same to obtain suitable residual solvent levels.

Thus according to another aspect of the invention, unexpectedly we have found that by dissolving ziprasidone free base in polar organic solvents such as 1-methyl-2-pyrrolidinone (NMP), for example, or even when ziprasidone free base is simply in suspension in medium-polarity organic solvents or a mixture of solvents such as lower alcohols, methyl isobutyl ketone (MIBK), etc., and then treating the solution or suspension, as the case may be, with a solution of anhydrous hydrogen chloride (preferably the hydrogen chloride is in a suitable organic solvent, such as isopropanol, ethyl ether, acetic acid, and ethanol), the ziprasidone hydrochloride anhydrate is directly obtained after drying.

Furthermore, the product obtained in this manner retains very small amounts of solvent and is obtained in high yield and purity. Thus the deficiencies encountered in the prior art are resolved by the use of this process.

Examples of medium polarity to polar organic solvents which are useful in the reaction of the present invention include, but are not limited to, cyclic or acyclic N-alkylated amides such as 1-methyl-2-pyrrolidinone (NMP), N,N-dimethylformamide (DMF), $C_1$ to $C_6$ alkyl alcohols such as methanol, ethanol, propanol, isopropanol, n-butanol; and $C_3$–$C_6$ alkyl ketone solvent such as methyl isobutyl ketone and their mixtures thereof.

DETAILED DESCRIPTION OF EMBODIMENTS OF THE INVENTION

The following examples illustrate the preparation of ziprasidone hydrochloride anhydrate and are not to be construed as limiting the scope of the invention in any manner.

EXAMPLE 1

Preparation of 5-[2-[4-(1,2-benzisothiazol-3-yl)-1-piperazinyl]ethyl]-6-chloro-1, 3-dihydro-2H-indol-2-one hydrochloride anhydrate.

To a flask equipped with magnetic stirrer, thermometer and nitrogen inlet was added 5-(2-(4-(1,2-benzisothiazol-3-yl)-1-piperazinyl)ethyl)-6-chloro-1,3-dihydro-2H-indol-2-one free base (5.0 g) and ethanol (100 mL) and the suspension was stirred at 20–25° C. under nitrogen. A 20.5% anhydrous solution of hydrogen chloride in isopropanol (6.45 g) was added and the mixture was stirred for about 24 h. The product was collected by filtration on a Buchner funnel. The filter cake is rinsed with 3×10 mL of ethanol at 20–25° C. and transferred to a drying oven and dried in vacuo at 65–70° C. for about 24 h., then at 70–75° C. for another 24 h. This afforded 5.27 g of anhydrous ziprasidone hydrochloride. The material contained a small amount of residual ethanol, 0.7% determined by NMR. The IR and powder X-ray diffractogram matched that of the desired anhydrous product as depicted in U.S. Pat. No. 5,312,925.

EXAMPLE 2

Preparation of 5-[2-[4-(1,2-benzisothiazol-3-yl)-1-piperazinyl]ethyl]-6-chloro-1, 3-dihydro-2H-indol-2-one hydrochloride anhydrate.

To a flask equipped with magnetic stirrer, thermometer and nitrogen inlet was added 5-(2-(4-(1,2-benzisothiazol-3-yl)-1-piperazinyl)ethyl)-6-chloro-1,3-dihydro-2H-indol-2-one free base (5.0 g) and methyl isobutyl ketone (100 mL) and the suspension was stirred at 20–25° C. under nitrogen. A 20.5% anhydrous solution of hydrogen chloride in isopropanol (6.45 g) was added and the mixture was stirred for about 24 h. The product was collected by filtration on a Buchner funnel. The filter cake is rinsed with 3×10 mL of methyl isobutyl ketone at 20–25° C. and transferred to a drying oven and dried in vacuo at 65–70° C. for about 24 h. This afforded 5.25 g of anhydrous ziprasidone hydrochloride. The material contained 0.52% of residual methyl isobutyl ketone, as determined by NMR.

EXAMPLE 3

Preparation of 5-[2-[4-(1,2-benzisothiazol-3-yl)-1-piperazinyl]ethyl]-6-chloro-1, 3-dihydro-2H-indol-2-one hydrochloride anhydrate.

To a 3-necked flask equipped with mechanical stirrer, thermometer and nitrogen inlet was added 5-(2-(4-(1,2-benzisothiazol-3-yl)-1-piperazinyl)ethyl)-6-chloro-1,3-dihydro-2H-indol-2-one free base (5.0 g) and 1-methyl-2-pyrrolidinone (60 mL) under nitrogen and the suspension was warmed up to 35–40° C. to dissolution. The flask was cooled to about 25° C. A 20.5% anhydrous solution of hydrogen chloride in isopropanol (6.45 g) was added and the mixture was stirred at about 25° C. for about 3 h. The product was collected by filtration on a Buchner funnel. The filter cake is rinsed twice with 10 mL of isopropanol at 20–25° C. and the damp cake transferred to a flask equipped with magnetic stirrer and nitrogen inlet. Isopropanol was added (30 mL) and the suspension stirred at 20–25° C. for about 2 h. The product was collected by filtration on a Buchner funnel. The filter cake is rinsed with 3×10 mL of isopropanol at 20–25° C. and transferred to a drying oven and dried in vacuo at 70–75° C. for 43 h. This afforded 4.52 g of anhydrous ziprasidone hydrochloride. The material contained 3.1% and 0.26% of residual NMP and IPA, respectively as determined by NMR.

While the foregoing provides a detailed description of examples of the invention, it is to be understood that the descriptions are illustrative only and not in a limiting sense. Furthermore, as many changes can be made to the examples without departing from the scope of the invention, it is intended that all material contained in the examples be interpreted as illustrative of the invention and not in a limiting sense.

The embodiments of the invention in which an exclusive property or privilege is claimed are as follows:

1. A process for the preparation of ziprasidone hydrochloride anhydrate comprising the steps of:
   (i) mixing ziprasidone free base in a medium polarity to polar organic solvent selected from the group consisting of cyclic and acyclic N-alkylated amides, $C_1$ to $C_6$ alkyl alcohol, $C_3$–$C_6$ alkyl ketone solvent and mixtures thereof;

(ii) adding hydrogen chloride;

(iii) stirring the reaction mixture for a sufficient amount of time to obtain complete ziprasidone hydrochloride formation; and thereafter (iv) isolating ziprasidone hydrochloride anhydrate and drying same to obtain suitable residual solvent levels.

2. The process of claim 1, wherein the a cyclic N-alkylated amide is N,N-dimethyl formamide.

3. The process of claim 1, wherein the cyclic N-alkylated amide is 1-methyl-2-pyrrolidinone.

4. The process of claim 1, wherein the $C_1$ to $C_6$ alkyl alcohol is further selected from the group consisting of methanol, ethanol, propanol, isopropanol, n-butanol and mixtures thereof; and wherein the $C_3$ to $C_6$ alkyl ketone is further selected from the group consisting of methyl isobutyl ketone, methyl isopropyl ketone and mixtures thereof.

5. The process of claim 1 or 4, wherein said addition of hydrogen chloride is performed in a suitable organic solvent selected from the group consisting of isopropanol, ethyl ether, acetic acid and ethanol.

6. The process of claim 2, wherein said addition of hydrogen chloride is performed in a suitable organic solvent selected from the group consisting of isopropanol, ethyl ether, acetic acid and ethanol.

7. The process of claim 3, wherein said addition of hydrogen chloride is performed in a suitable organic solvent selected from the group consisting of isopropanol, ethyl ether, acetic acid and ethanol.

8. The process of claim 1 or 4, wherein Step (i) takes place at a temperature between 0° C. and 60° C.

9. The process of claim 2, wherein Step (i) takes place at a temperature between 0° C. and 60° C.

10. The process of claim 3, wherein Step (i) takes place at a temperature between 0° C. and 60° C.

11. The process of claim 6, wherein Step (i) takes place at a temperature between 0° C. and 60° C.

12. The process of claim 7, wherein Step (i) takes place at a temperature between 0° C. and 60° C.

* * * * *